United States Patent [19]

Petersen

[11] 4,088,757
[45] May 9, 1978

[54] 4 ALPHA- AND 4 BETA-AMINO-4-DESOXYOLEANDRINS, AND PHARMACEUTICAL COMPOSITION CONTAINING SAME

[75] Inventor: Rudolf Petersen, Wohltorf, Germany

[73] Assignee: Beiersdorf Aktiengesellschaft, Hamburg, Germany

[21] Appl. No.: 758,993

[22] Filed: Jan. 13, 1977

[30] Foreign Application Priority Data

Jan. 28, 1976 Germany .............................. 2603046

[51] Int. Cl.² .................... A61K 31/705; C07J 19/00
[52] U.S. Cl. ........................................ 424/182; 536/5; 536/7
[58] Field of Search ................. 536/5, 7; 424/182

[56] References Cited

U.S. PATENT DOCUMENTS 3,898,331  8/1975  Petersen ................................. 536/7
3,914,213  10/1975  Stache et al. ........................... 536/7

Primary Examiner—Johnnie R. Brown
Attorney, Agent, or Firm—Bierman & Bierman

[57] ABSTRACT

The present invention relates to 4' amino- 4'desoxyoleandrins of the following formula (I)

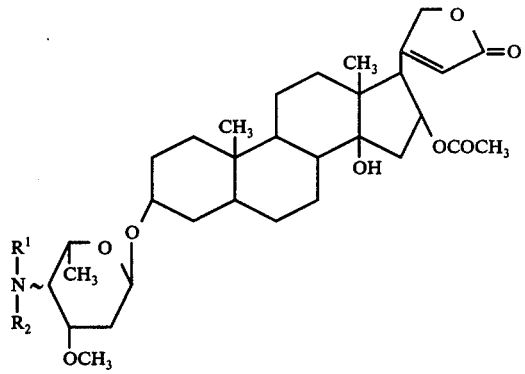

in which $R^1$ and $R^2$ may be the same or different and represent hydrogen or a lower alkyl group with 1 to 4 carbon atoms or $R^1$ and $R^2$ together with the nitrogen atom form a pyrrolidino, piperidino, or morpholino radical; as well as the physiologically compatible acid addition salts thereof.

These compounds possess positive inotropic cardiac activity and are useful in cases of renal insufficiency.

6 Claims, No Drawings

4 ALPHA- AND 4 BETA-AMINO-4-DESOXYOLEANDRINS, AND PHARMACEUTICAL COMPOSITION CONTAINING SAME

This application claims the priority of German Patent Application No. P 26 03 046.6, filed Jan. 28, 1976.

The present invention relates to 4'amino-4'desoxy-oleandrins of the following formula (I)

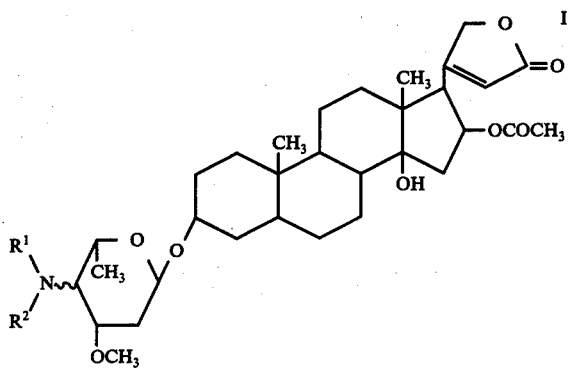

in which $R^1$ and $R^2$ may be the same or different and represent hydrogen or a lower alkyl group with 1 to 4 carbon atoms or $R^1$ and $R^2$ together with the nitrogen atom form a pyrrolidino, piperidino, or morpholino radical; as well as they physiologically compatible acid addition salts thereof.

These new substances, whether used as the free amine base or the salt possess valuable pharmacological properties; in particular, they have positive-inotropic cardiac activity. These compounds have remarkably good resorption and are preferentially eliminated via the biliary tract. They are excreted from the bile duct into the intestines, thereby permitting their use in cases of renal insufficiency.

Tests were run comparing the inotropic effect and method of elimination of 4'amino-4'-desoxy-oleandrin and digoxin. The results are set forth below.

1. The elimination rate of both drugs in the cat was tested by intravenously injecting a fixed amount of the drugs into the cat and recording the amount of tritium-marked drug appearing in the urine and feces. The results are stated as a percentage of the activity of the tritium-marked glycoside originally injected. The following table clearly indicates that digoxin is preferentially eliminated by the renal system and that 4'amino-4'-desoxy-oleandrin is preferentially eliminated by the biliary system.

| Drug | Renal Elimination | Biliary Elimination |
| --- | --- | --- |
| 4'-amino-4'-desoxy-oleandrin | 2.5% | 11.1% |
| digoxin | 6.3% | 4.7% |

2. The inotropic effect of both drugs was tested on the papillary muscle of the guinea pig in vitro. The muscle was connected to a recording device and then placed in a bath of 0.1% solution of the drug to be tested in a mixture of 40% ethanol and 60% water. This solution was gradually diluted with water and a dosage versus contraction graph plotted. The amount of drug necessary to increase the contractile force of the muscle by 50% ($ED_{50}$) was then calculated. The results are set forth below.

| Drug | $ED_{50}$ (gamma/ml) |
| --- | --- |
| 4'-amino-4'-desoxy-oleandrin | 0.13 |
| digoxin | 1.10 |

The compounds of the present invention may be used in the form of free amine bases or in the form of acid addition salts. They may be mixed with pharmacologically compatible solid or liquid vehicles and diluents. They may be used as solutions for injections and may be used in oral dosage forms such as dragees, pills or tablets.

The compounds of the general Formula I can be manufactured using well-known reaction mechanisms according to the following methods:

a. By transformation of 4'-dehydro-oleandrin (Formula II) into the oxime of Formula III and reduction with a suitable reducing agent to form the two primary amines, in which $R^1$ and $R^2$ are hydrogen, and b. By the reductive amination of 4'dehydro-oleandrin (II) to obtain the primary secondary and tertiary amine products.

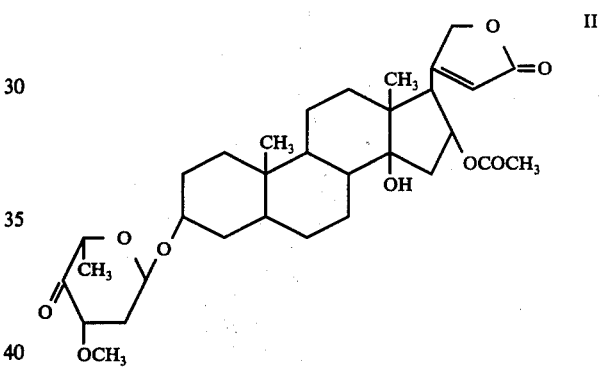

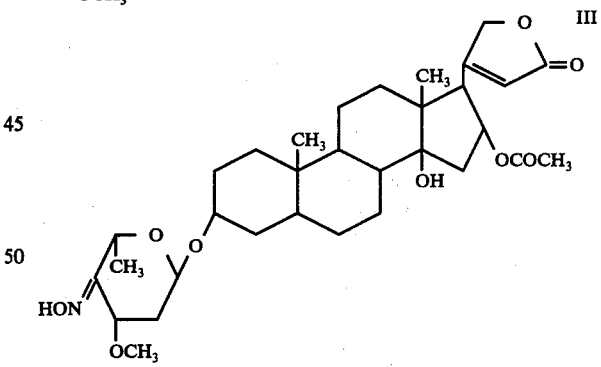

In the synthesis of the amino-oleandrins via said processes, the two possible isomers form at the $C_4$ atom on the sugar part of the molecule. The two isomers can be separated by column chromatography using a silica gel column. Successive chloroform mixtures having an increasing methanol content are used as eluant.

The oxidation of oleandrin to 4'dehydro-oleandrin can be effected with oxidizing agents known in sugar chemistry. Particularly suitable for this purpose are dimethyl sulfoxide and chromium (VI)-oxide.

In order to transform the 4'dehydro-oleandrin into the oxime of Formula III, either hydroxylamine or the salts thereof are used. If subsequently an aluminum amalgam is used for the reduction to the primary amine, the oxime is dissolved in a mixture of dioxane and lower alcohols, and ammonium chloride and aqueous ammonia are added. Preferably, the reaction is carried out at room temperature and is run for a period of 8 to 10 days. The separation of the by-products and the division of the isomers can be carried out using a column chromatograph with a silica gel column. Successive mixtures of chloroform having an increasing methanol content (1–5%) are used as the eluant.

The primary, secondary and tertiary amines can be synthesized from the direct transformation of 4'-dehydro-oleandrin into 4'amino-4-desoxy-oleandrins by the reduction of the oxo-compound in the presence of the salts of the respective amines, preferably the hydrochlorides. Preferably, when the primary amine is desired, ammonium acetate is used. Lower aliphatic alcohols, in particular methanol, are used as solvents. The reaction is run at temperatures between 0° and 50° C for a period of 1 to 5 days. $NaBH_3CN$ is the preferred reducing agent because the lactone ring of the steroid is not destroyed by its use.

The preparation of the new compounds according to the present invention is described more fully in the following examples:

EXAMPLE 1 a. The oxime of 4'-dehydro-oleandrin 4.6g (8m moles) of 4'-dehydro-oleandrin are dissolved in 800 ml of 96% ethanol with the application of heat. After cooling, 3.0 g (43.5 m moles) hydroxylamoine. HCl and then 6.6 g (80.5 m moles) sodium acetate (anhydrous) are added. After standing at room temperature for 20 hours, 2 liters of chloroform are added. The mixture is extracted three times with 400 ml of water each time. The chloroform phases are dried with sodium sulfate and the solvent is removed under a vacuum. A colorless oil remains which is crystallized by the addition of 40 ml methanol. The yield obtained was 3.8 g.

b. Reduction to 4'-amino-4'-desoxy-oleandrin 2.g (3.4 m moles) of oxime are dissolved in a mixture of 100 ml of dioxane, 120 ml of ethanol, 40 ml of methanol and 45 ml of water. To this mixture are added 30 g of freshly amalgamated aluminum chips, 1 g $NH_4Cl$ and 1.5ml of concentrated ammonia solution. This mixture is left standing for 8 days at room temperature.

The gelatinous mass that has formed is then diluted with 150 ml ethanol and 50 ml methanol and suction-filtered over kieselguhr and washed again with a mixture of methanol and ethanol. The combined filtrates are concentrated below 40° C under a vacuum. The residue is partitioned between water and chloroform and the aqueous phase is extracted twice with chloroform. After the chloroform phase is dried, the solvent is evaporated under a vacuum and the residue purified in a silica gel column. Chloroform, with increasing quantities (1 to 5%) of methanol, is used as the eluant.

The two isomers can also be separated on a thin layer plate (SIF, Riedel de Haen), using chloroform and methanol in a ratio of 92 : 8. The Rf value, melting point and nitrogen content were determined for each isomer and the results are set forth below:

Isomer # 1
Rf value: 0.33

-continued

Mp: 121–126° C
N content calculated: 2.36%, found: 2.15%
Isomer # 2
Rf value: 0.19
Mp: 134–136° C
N content calculated: 2.36%, found 2.19%

EXAMPLE 2

4'amino-4'-desoxy-oleandrin 2.3 g (4 m moles) of 4'-dehydro-oleandrin are suspended along with 6.08 g (80 m moles) of dried ammonium acetate and 0.38 g (6 m moles) of $NaBH_3CN$ in 100 ml of absolute methanol and stirred after the addition of a 2 g molecular sieve (4 Ang. pearl form, MERCK) for 2 days at room temperature. After filtration, the solvent is removed under a vacuum and the residue is admixed and shaken with 50 ml of water and 50 ml chloroform. After the aqueous phase is extracted twice with chloroform, the combined chloroform phases are then dried with sodium sulfate and the solvent is removed under a vacuum. Separation of the by-products and isolation of the two isomers is carried out by column chromatography using a silica gel column and chloroform and methanol as described in Example 1. 1.8 f of the isomer mixture of the desired amine are obtained having the following values.

Isomer # 1
Rf value: 0.31
Mp of the amine: 120–125° C
N analysis: Calculated 2.36, Found 2.29
Isomer # 2
Rf value: 0.20
Mp of the amine: 135–137° C
N analysis: Calculated 2.36, Found 2.28

The two isomers can also be separated via thin layer chromatography as used in Example 1.

EXAMPLE 3

4'-ethylamino-4'-desoxy-oleandrin 1.15 g (2 m moles) 4'-dehydro-oleandrin, 324 mg (4 m moles) ethylamine. HCl, 190 mg (3 m moles) $NaBH_3CN$ and 1 g of molecular sieve are suspended in 50 ml or absolute methanol and agitated at room temperature for 48 hours. After filtering, the methanol is evaporated under a vacuum and the residue is partitioned between 50 ml of water and 50 ml of chloroform and the water phase is extracted twice with chloroform. After drying the chloroform phases with $Na_2SO_4$, the amine is separated via a silica gel column chromatograph.

The compound obtained was tested and the following values were obtained:

Rf value: 0.35

Mp of the isomer mixture: 125°–132° C (with decomposition)

N content (calculated with 2 $H_2O$) calculated: 2.14%, found 2.20%

The following amines were synthesized using procedures analogous to those of Example 3.

4'-methylamino-4'-desoxy-oleandrin

Isomer # 1
Rf value: 0.16
Mp: 112–115° C
N content calculated: 2.37%, found 2.13%

-continued

4'-methylamino-4'-desoxy-oleandrin

Isomer # 2

Rf value: 0.45

Mp: 123–125° C

N content calculated 2.37% found 2.22%

4'-dimethylamino-4'-desoxy-oleandrin

Rf value: 0.55

Mp of the isomer mixture: 173–177° C

N content: calculated 2.32%, found 2.32%

What we claim is:

1. 4'-alpha- and 4'beta-amino-4'-desoxy-oleandrins of the formula:

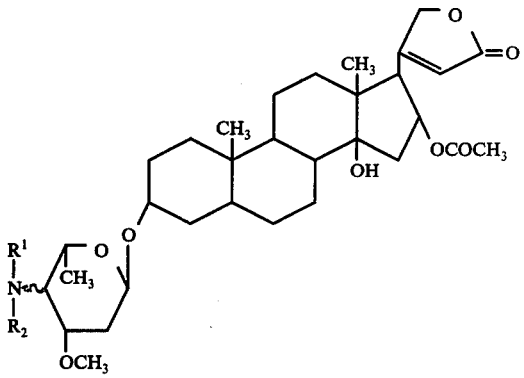

wherein $R^1$ and $R^2$, which may be the same or different, are individually selected from the group consisting of hydrogen, or a lower alkyl group with 1-4 carbon atoms, or $R^1$ and $R^2$ together with the nitrogen atom form pyrrolidino, piperidino, or morpholino; and the physiologically compatible acid addition salts thereof.

2. The compound as recited in claim 1 wherein $R^1$ and $R^2$ are hydrogen.

3. The compound as recited in claim 1 wherein $R^1$ is hydrogen and $R^2$ is ethyl.

4. The compound as recited in claim 1 wherein $R^1$ is methyl and $R^2$ is hydrogen.

5. The compound as recited in claim 1 wherein $R^1$ and $R^2$ are methyl.

6. A pharmaceutical composition containing an effective amount of at least one 4'-amino-4'desoxy-oleandrin according to claim 1 and a physiologically compatible substance.

* * * * *